United States Patent
Alchemy et al.

(10) Patent No.: US 11,853,973 B1
(45) Date of Patent: *Dec. 26, 2023

(54) METHOD OF AND SYSTEM FOR EXECUTING AN IMPAIRMENT REPAIR PROCESS

(71) Applicant: Alchemy Logic Systems, Inc., Santa Rosa, CA (US)

(72) Inventors: John William Alchemy, Santa Rosa, CA (US); Bruce Brandon Wilson, Woodbury, MN (US)

(73) Assignee: Alchemy Logic Systems, Inc., Santa Rosa, CA (US)

( * ) Notice: Subject to any disclaimer, the term of this patent is extended or adjusted under 35 U.S.C. 154(b) by 983 days.

This patent is subject to a terminal disclaimer.

(21) Appl. No.: 15/415,581

(22) Filed: Jan. 25, 2017

Related U.S. Application Data

(60) Provisional application No. 62/367,010, filed on Jul. 26, 2016.

(51) Int. Cl.
  *G06Q 10/1057* (2023.01)
  *G16H 10/60* (2018.01)
  *G16H 40/63* (2018.01)

(52) U.S. Cl.
  CPC ......... *G06Q 10/1057* (2013.01); *G16H 10/60* (2018.01); *G16H 40/63* (2018.01)

(58) Field of Classification Search
  CPC .... G06Q 40/08; G06Q 10/06; G06Q 10/0639; G06Q 50/265; G06Q 10/00;
  (Continued)

(56) References Cited

U.S. PATENT DOCUMENTS

| 4,916,611 A | 4/1990 | Doyle, Jr. et al. |
| 4,987,538 A | 1/1991 | Johnson et al. |

(Continued)

FOREIGN PATENT DOCUMENTS

| CA | 2707207 A1 | 6/2009 |
| WO | WO2008006117 A2 | 1/2008 |
| WO | WO2018224937 A1 | 12/2018 |

OTHER PUBLICATIONS

State of California Department of Industrial Relations Division of Workers' Compensation "Physician's Guide to Medical Practice in the California Workers' Compensation System," Fourth Ed., 2016, 137 pages (Year: 2016).*

(Continued)

*Primary Examiner* — Rachel L. Porter
(74) *Attorney, Agent, or Firm* — Haverstock & Owens, A Law Corporation

(57) ABSTRACT

A method and system enhances the execution of the telemedicine impairment repair process (IRP) to claim closure by assisting all stakeholders by monitoring the process and reminding the stakeholders of the stakeholder roles and responsibilities to maintain a prudent time frame for the reported injury and/or illness. The method of and system for executing an impairment repair process addresses flaws in the current process by implementing timing guided by legislation and best medical practice. Key aspects of the impairment repair process are addressed to ensure prudent timing by assuring accuracy of claim development, monitoring, and initiating communication to closure. The process is implemented in multiple stages including, assessment, documentation, prescribed treatment, and analysis of outcome.

17 Claims, 13 Drawing Sheets

(58) Field of Classification Search
CPC ......... G06Q 10/06393; G06Q 30/0283; G06Q 40/00; G06Q 40/02; G06Q 40/12; G06Q 50/04; G06Q 10/08; G06Q 10/20; G06Q 30/0206; G06Q 40/06; G06Q 10/047; G06Q 10/063; G06Q 10/0635; G06Q 10/06395; G06Q 20/145; G06Q 50/08

See application file for complete search history.

(56) References Cited

U.S. PATENT DOCUMENTS

| | | | | |
|---|---|---|---|---|
| 5,182,705 | A | 1/1993 | Barr et al. | |
| 5,367,675 | A | 11/1994 | Cheng et al. | |
| 5,517,405 | A | 5/1996 | McAndrew et al. | |
| 5,544,044 | A | 8/1996 | Leatherman | |
| 5,613,072 | A | 3/1997 | Hammond et al. | |
| 5,778,345 | A | 7/1998 | McCartney | |
| 5,911,132 | A | 6/1999 | Sloane | |
| 6,003,007 | A | 12/1999 | DiRienzo | |
| 6,065,000 | A | 5/2000 | Jensen | |
| 6,604,080 | B1 | 8/2003 | Kern | |
| 6,810,391 | B1 | 10/2004 | Birkhoelzer et al. | |
| 6,865,581 | B1 | 3/2005 | Cloninger, Jr | |
| 6,954,730 | B2 | 10/2005 | Lau et al. | |
| 6,957,227 | B2 | 10/2005 | Fogel et al. | |
| 7,337,121 | B1 | 2/2008 | Beinat | |
| 7,401,056 | B2 | 7/2008 | Kam | |
| 7,440,904 | B2 | 10/2008 | Hasan et al. | |
| 7,475,020 | B2 | 1/2009 | Hasan et al. | |
| 7,509,264 | B2 | 3/2009 | Hasan et al. | |
| 7,630,911 | B2 | 12/2009 | Kay | |
| 7,630,913 | B2 | 12/2009 | Kay | |
| 7,707,046 | B2 | 4/2010 | Kay | |
| 7,707,047 | B2 | 4/2010 | Hasan et al. | |
| 7,778,849 | B1 | 8/2010 | Hutton | |
| 7,813,944 | B1 | 10/2010 | Luk | |
| 7,870,011 | B2 | 1/2011 | Kay | |
| 7,904,309 | B2 | 3/2011 | Malone | |
| 7,930,190 | B1 | 4/2011 | Milanovich | |
| 7,949,550 | B2 | 5/2011 | Kay | |
| 7,970,865 | B2 | 6/2011 | DeCesare et al. | |
| 8,019,624 | B2 | 9/2011 | Malone | |
| 8,041,585 | B1 | 10/2011 | Binns et al. | |
| 8,065,163 | B2 | 11/2011 | Morita et al. | |
| 8,069,066 | B2 | 11/2011 | Stevens et al. | |
| 8,185,410 | B2 | 5/2012 | Brigham | |
| 8,301,575 | B2 | 10/2012 | Bonnet et al. | |
| 8,346,573 | B2 | 1/2013 | Glimp et al. | |
| 8,489,413 | B1 | 7/2013 | Larson et al. | |
| 8,489,424 | B2 | 7/2013 | Hasan et al. | |
| 8,510,134 | B1 | 8/2013 | Sweat et al. | |
| 8,527,303 | B2 | 9/2013 | Kay | |
| 8,615,409 | B1 | 12/2013 | McKown | |
| 8,630,878 | B1 | 1/2014 | Kravets et al. | |
| 8,725,524 | B2 | 5/2014 | Fano | |
| 8,725,538 | B2 | 5/2014 | Kay | |
| 8,751,252 | B2 | 6/2014 | Chamberlain | |
| 8,751,263 | B1 | 6/2014 | Cave et al. | |
| 8,751,266 | B2 | 6/2014 | Stang | |
| 8,775,216 | B1 | 7/2014 | Amick et al. | |
| 8,864,663 | B1 | 10/2014 | Kahn et al. | |
| 8,868,768 | B2 | 10/2014 | Sokoryansky | |
| 8,888,697 | B2 | 11/2014 | Bowman et al. | |
| 8,900,141 | B2 | 12/2014 | Smith et al. | |
| 8,910,278 | B2 | 12/2014 | Davne et al. | |
| 8,930,225 | B2 | 1/2015 | Morris | |
| 8,959,027 | B2 | 1/2015 | Kusens | |
| 8,954,339 | B2 | 2/2015 | Schaffer | |
| 9,002,719 | B2 | 4/2015 | Tofte | |
| 9,015,055 | B2 | 4/2015 | Tirinato et al. | |
| 9,020,828 | B2 | 4/2015 | Heidenreich | |
| 9,229,917 | B2 | 1/2016 | Larcheveque | |
| 9,710,600 | B1 | 7/2017 | Dunleavy | |
| 2001/0027331 | A1 | 10/2001 | Thompson | |
| 2001/0044735 | A1 | 11/2001 | Colburn | |
| 2001/0053984 | A1 | 12/2001 | Joyce | |
| 2002/0069089 | A1 | 6/2002 | Arkin | |
| 2002/0077849 | A1 | 6/2002 | Baruch | |
| 2004/0044546 | A1* | 3/2004 | Moore | G16H 50/20 705/2 |
| 2005/0060184 | A1 | 3/2005 | Wahlbin | |
| 2005/0177403 | A1 | 8/2005 | Johnson | |
| 2005/0256744 | A1* | 11/2005 | Rohde | G06Q 10/00 705/2 |
| 2006/0161456 | A1 | 7/2006 | Baker | |
| 2006/0287879 | A1* | 12/2006 | Malone | G09B 19/00 705/2 |
| 2007/0118406 | A1* | 5/2007 | Killin | G16H 20/30 482/8 |
| 2007/0250352 | A1 | 10/2007 | Tawil | |
| 2008/0046297 | A1 | 2/2008 | Shafer | |
| 2008/0133297 | A1 | 6/2008 | Schmotzer | |
| 2008/0154672 | A1 | 6/2008 | Skedsvold | |
| 2008/0183497 | A1 | 7/2008 | Soon-Shiong | |
| 2009/0099875 | A1 | 4/2009 | Koenig | |
| 2010/0042435 | A1 | 2/2010 | Kay | |
| 2010/0106520 | A1 | 4/2010 | Kay | |
| 2010/0106526 | A1 | 4/2010 | Kay | |
| 2010/0114609 | A1 | 5/2010 | Duffy, Jr. et al. | |
| 2010/0217624 | A1 | 8/2010 | Kay | |
| 2010/0240963 | A1 | 9/2010 | Brighman | |
| 2011/0077980 | A1 | 3/2011 | Kay | |
| 2011/0077981 | A1 | 3/2011 | Kay | |
| 2011/0145012 | A1 | 6/2011 | Nightingale | |
| 2011/0161115 | A1 | 6/2011 | Hampton | |
| 2011/0257919 | A1 | 10/2011 | Reiner | |
| 2011/0257993 | A1 | 10/2011 | Shahani | |
| 2011/0313785 | A1 | 12/2011 | Lash | |
| 2011/0313912 | A1 | 12/2011 | Teutsch | |
| 2012/0022884 | A1 | 1/2012 | Chillemi | |
| 2012/0102026 | A1 | 4/2012 | Fortune | |
| 2012/0130751 | A1 | 5/2012 | McHugh | |
| 2012/0232924 | A1 | 9/2012 | Bingham | |
| 2012/0245973 | A1 | 9/2012 | Pandya | |
| 2012/0278095 | A1 | 11/2012 | Homchowdhury | |
| 2012/0284052 | A1 | 11/2012 | Saukas | |
| 2013/0024214 | A1 | 1/2013 | Schoen et al. | |
| 2013/0132122 | A1 | 5/2013 | Walsh | |
| 2014/0052465 | A1* | 2/2014 | Madan | G16H 50/50 705/2 |
| 2014/0058763 | A1 | 2/2014 | Zizzamia | |
| 2014/0073486 | A1 | 3/2014 | Ahmed | |
| 2014/0136216 | A1* | 5/2014 | Beebe | G06Q 40/08 705/2 |
| 2014/0172439 | A1 | 6/2014 | Conway et al. | |
| 2014/0201213 | A1 | 7/2014 | Jackson | |
| 2014/0249850 | A1 | 9/2014 | Woodson | |
| 2014/0278479 | A1 | 9/2014 | Wang et al. | |
| 2014/0278830 | A1 | 9/2014 | Gagne | |
| 2014/0303993 | A1 | 10/2014 | Florian | |
| 2014/0379364 | A1 | 12/2014 | Liu et al. | |
| 2015/0019234 | A1 | 1/2015 | Cooper | |
| 2015/0221057 | A1 | 8/2015 | Raheja et al. | |
| 2015/0235334 | A1 | 8/2015 | Wang et al. | |
| 2015/0242585 | A1 | 8/2015 | Spiegel | |
| 2015/0278462 | A1 | 10/2015 | Smoley et al. | |
| 2015/0286792 | A1 | 10/2015 | Gardner | |
| 2015/0324523 | A1 | 11/2015 | Parthasarathy et al. | |
| 2016/0063197 | A1 | 3/2016 | Kumetz | |
| 2016/0125544 | A1 | 5/2016 | Edwards | |
| 2016/0283676 | A1 | 9/2016 | Lyon | |
| 2016/0292371 | A1* | 10/2016 | Alhimiri | G06Q 10/00 |
| 2017/0140489 | A1 | 5/2017 | Ziobro | |
| 2017/0154374 | A1 | 6/2017 | Iglesias | |
| 2017/0177810 | A1 | 6/2017 | Fulton | |
| 2017/0228517 | A1 | 8/2017 | Saliman | |
| 2017/0255754 | A1 | 9/2017 | Allen | |
| 2017/0316424 | A1* | 11/2017 | Messana | G06Q 50/265 |
| 2017/0352105 | A1 | 12/2017 | Billings | |
| 2018/0025334 | A1 | 1/2018 | Pourfallah | |
| 2018/0279919 | A1 | 10/2018 | Bansbach | |
| 2019/0065686 | A1 | 2/2019 | Crane | |
| 2020/0126645 | A1* | 4/2020 | Robbins | H04L 63/0861 |

(56) References Cited

U.S. PATENT DOCUMENTS

2020/0279622 A1    9/2020   Heywood
2020/0286600 A1    9/2020   De Brouwer

OTHER PUBLICATIONS

"CA DWC Releases 4th Edition of Physician's Guide to Medical Practice in CA WC," Workwcompwire, Apr. 5, 2016, https://www.workcompwire.com/2016/04/ca-dwc-releases-4th-edition-of-physicians-guide-to-medical-practice-in-ca-wc/ (Year: 2016).*

Park, Y., Butler, R. J. (2000). Permanant Partial Disability Awards and Wage Los. Journal of Risk and Insurance, 67(3), 331. Retrieved from https"//dialog.proquest.com/professional/docview/769439682, Year 2000, 18 pages.

State of California Department of Industrial Relations Division of Workers' Compensation, Physician's Guide to Medical Practice in the California Workers' Compensation System, Fourth Edition, 2016, 137 pages.

Cocchiarella, Linda and Andersson, Gunnar B. J., Guides to the Evaluation of Permanent Impairment, 2001, Fifth Edition, American Medical Association, 618 pages.

In B. Pfaffenberger, Webster's new World& Trade; Computer Dictionary(10th ed). Houghton Mifflin Harcourt, Credo reference:https://search.credoreference.com/content/entry/webster.com/database(year 2003).

"Physician's Guide to Medical Practice in the California Worker's Compensation System", 2016, State of California Department of Industrial Relations Division of Worker's Compensation, 4th ed., all pages. (Year 2016).

Rondinelli, Robert D., Guides to the Evaluation of Permanent Impairment, 2008 Sixth Edition, American Medical Association.

Hakkinen, Arja, et al. "Muscle strength, pain, and disease activity explain individual subdimensions of the Health Assessment Questionaire disability index, especially in women with rheumatoid arthritis." Annals of the rheumatic diseases 65.1 (2006): 30-34. (Year: 2006).

Programming languages. (2004). In W. S. Bainbridge (Ed)., Berkshire encylopedia of human-computer interaction. Berkshire Publishing Group. Credo Reference: https://search.credoreference.com/content/entry/berkencyhci/programming_languages/0? institutionid=743 (Year: 2004), 5 pages.

Ammendolia C. Cassidy D., Steensta I, et al. Designing a Workplace Return-to Work Program for Occupational Low Back Pain: an intervention mapping approach. BMC Musculoskelet Disord. 2009;10:65. Published Jun. 9, 2009. doi: 10.1186/1471-2474-10-65 (Year; 2009). 10 pages.

Wasiak, Radoslaw, et al. "Measuring Return To Work." Journal of Occupational Rehabilitation 17.4 (2007): 766-781. (Year: 2007). 16 pages.

CA Medical Treatment Utilization Schedule, Proposed Chronic Pain Medical Treatment Guidelines, Jun. 2008, 83 pages.

* cited by examiner

METHOD OF AND SYSTEM FOR EXECUTING AN IMPAIRMENT REPAIR PROCESS

RELATED APPLICATIONS

This Patent Application claims priority under 35 U.S.C. 119(e) of the U.S. provisional patent application, Application No. 62/367,010, filed on Jul. 26, 2016, and entitled "METHOD TO EXECUTE IMPAIRMENT REPAIR PROCESS," which is hereby incorporated in its entirety by reference.

FIELD OF THE INVENTION

The present invention is generally directed to telemedicine. More specifically, the present invention is directed to a method and system for addressing the communication break down in the existing worker's compensation claim process.

BACKGROUND OF THE INVENTION

As defined by the California State Assembly Bill 415 2290.5, which is hereby incorporated by reference, Telehealth or Telemedicine is the mechanism by which healthcare services and public health information and communication technologies deliver and facilitate the diagnosis, consultation, treatment, education, care management, and self-management of a patient's health care while the patient is at the originating site and the health care provider is at a distant site. Telehealth facilitates patient self-management and caregiver support for patients and includes synchronous interactions and asynchronous store and forward transfers. The US Government and Human Services is directed by Title 42, Public Health regarding its Telehealth and Telemedicine mechanisms. 42 CFR §§ 482.12, 482.22 and 485.616 are also hereby incorporated by reference.

Despite these regulations and codes, there is widespread confusion on the part of stakeholders as to who is the driver and what are the key deliverables of the Telemedicine process. Consequently, the current system frequently has significant time and delivery gaps, which results in wide variations in case duration. In a majority of these cases, the variations in case durations is from the absence of a central driver.

The absence of the central driver within the impairment repair process (IRP) is at first not obvious because legislation, such as that referenced above would seem to create clear roles and responsibilities. However, in practice, stakeholder roles are not so clear.

Some say that it should be the insurance company that drives the process. However, examination of cases in practice indicates that stakeholders, specifically the case officer or an agent employed by the insurance company (e.g. independent utilization review services), frequently delay the IRP. Specifically, delays can occur as the stakeholders remove designated therapies or prescribed treatments from the repair process because a review indicates the therapies and/or prescribed treatments may not be "supported by medical evidence" or are "under current medical investigation."

Cases can also be delayed when the case officer or agent challenges the "availability" of the treatment within the provider network. The basis of the rejection can be from a perceived cost hike due to the lack of a contract between the insurer and the provider. However, later review often indicates that the cost of the delay of treatment is greater than simply approving the treatment in the first place. The greatest cost burden can be to the insurance provider arising from delays in settling the claim. These increased costs are ultimately passed to the other stakeholders, including the employer, and a resulting loss of economic benefit to society.

The patient, as a stakeholder, is rarely, if ever, equipped with the necessary working knowledge of the medical system to drive the IRP. Yet, it is the patient as the stakeholder, with arguably the greatest reason for prudent discipline in pursuing therapies and treatments. After an injury, the faster the body is repaired, the easier it is for the physiology of the body to return to normal and the easier it is for the patient to return to a normal life and work routine.

Similarly, the physician typically does not drive the process either. With numerous patients and cases, a physician does not have the authority or resources to marshal the process. The physician establishes what must be done regarding the patient. While the physician is the gatekeeper of the medical portion of the process and determines the injury, therapy and stated outcome, establishing and maintaining timing protocols is not the responsibility nor role of the physician.

The physician and the physician's office have multiple critically timed functions. For example, an injured worker (the patient) must be scheduled and attend these visits (or have a plan for rescheduling). Additionally, the physician must perform a proper exam, deliver an accurate diagnosis, and complete a correct administrative document with treatment requests that is submitted in a timely fashion. If any of these functions is delayed, then the system begins to delay.

Some stakeholders within the IRP see the oversight board as the driver of the process. In most states, the oversight board is a combination of the executive and/or judiciary branches of the government. The most common scenario is that the oversight authority falls to the judiciary branch. For example, in California, this judiciary branch is the Division of Worker's Compensation (DWC) and has direct ties to the Department of Industrial Relations Branch (DIR) of the Governor's Office.

However, in actual execution the role of the judiciary is a passive one. The judiciary responds to the cases and data presented before it. The judiciary determines at what threshold of medical data the case is thought to be sufficient and adjudicate the claim. It may interpret the law to inform certain stakeholder responsibility, but the judiciary does not initiate the timing of events. The judges enforce the integrity of the IRP, but the limits of the medical and logistical part of the process are beyond their control.

It is the law that is thought to be the driver. In most jurisdictions (county, city, state), the law dictates the criteria and timing of events based on some established value set. Hence, it is the legislature at the behest of the people that establishes the timing guidelines for a prudent IRP. The failure happens where the societal and legislative guides are leveraged to an active driver of the IRP. The current reality is that there is no one person or entity that has the primary responsibility to follow and guide action throughout the IRP.

A central driver within the IRP is important because it is the insurance carrier and the employer that retain money to cover the cost of a claim. The problem is that neither the insurance carrier nor the employer know what the costs will be or when the costs will occur. This often occurs because there is a great variability in the other stakeholder's ability to understand the proper course of treatment as determined by the associative administrative rule set (ARS). This causes the stakeholder's to set aside a critical resource that can then not be used in the core business activities, thus reducing profitability.

Worker recovery and treatment and the timing of the recovery and treatment must have a prudent timing and level to assure the best outcome during the IRP. An employer is typically without an employee during the initial phase of case development. The quicker a case threshold is met and a Maximal Medical Improvement (MMI) is determined, the faster an employer can move forward with human resource decisions.

Additionally, the review and oversight boards and judges are flooded with cases. Consequently, any mechanism or intervention that shortens the IRP and/or makes case process more efficient also helps these oversight authorities.

As described above, each stakeholder can contribute to a failure of the IRP. Some examples of a failure are shown below.

Example 1

This first example is a common timing and function failure of the IRP. The injured worker does not report the injury and event, does not respond to requests for information or does not arrange appointments with the other stakeholders. The variance of motivations for not engaging the process tends to cause a presumption of innocence in the part of the process. Simply not knowing the laws and processes around the work related injury event give rise to anxiety, fear, or other reactions. Some common causes for non-responding workers, can be but are not limited to:
  transfer of a known claim
  administrative compliance issues
  "People aren't fessing up and doing what they should do"
  failed obligations
  Timed out for administrative reasons
  attorney advice
  employee fear of dismissal—injured worker not reporting incident
  "suspected but not confirmed" event Example 2

The second example involves rejected reports due to errors in the IRP, as a physician and/or clinician examines a worker for a potentially compensational medical injury or exposure. Such examples, are shown in U.S. patent application Ser. No. 14/996,067 to Alchemy et al., (hereinafter "the '067 Application"), which is hereby incorporated by reference. The IRP involves a clinician, which examines the worker for functional deficiencies as a result of, but not limited to, a work related injury event or illness.

Any errors in the IRP are carried forward in the worker compensation process to treatment, MMI potential, the need for prophylactics or braces, worker capability, re-training, compensation claims, and legal costs from challenged ratings, etc. Hence, small errors in the IRP evolve into much larger issues over time. Stakeholders such as employers, insurance companies, clinics, and the worker rely heavily on the impairment rating, whose quality is highly dependent on the evaluator's individual knowledge base and completeness of the clinical data set.

A lack of compliance, completeness or rigor, to the examination process can arise from numerous causes. Some examples can be, but are not limited to:

the clinician does not have adequate training in the process and unintentionally omit certain measurements or neglect to even examine for some other critical pathology
  the clinician after the the initial examination and discussion with a worker makes a subjective jump to an impairment rating, without the appropriate complete examination and clinical data to support the impairment value that has been assumed or estimated
  the clinician may not have an appreciation of the need for data replication to obtain statistical confidence in the measurement
  the clinician may be too limited on time to perform a rigorous examination—a perceived cost of the rigorous exam may be thought too expensive for the subjectively perceived level of the pathology (a "discharged as cured" process without a compliant history or physical exam, resulting in no access to future care)
  the clinician may also view sections of an ARS as "loop holes", excessive, confusing, or too clinically cumbersome to obtain.

Regardless of the reason, by omitting sections of the data set used for impairment rating, the clinician can effectively deteriorate or corrode the accuracy of a rating value, which in turn, can significantly alter the ultimate course and outcome of the claim to the stakeholders.

There are numerous reasons why a clinician may not perform the examination to the appropriate rigor, including intentional misrepresentation of the functional deficiencies. The clinician may also inadvertently, not paying attention, enter incorrect values. These causes have been described in the '067 Application and are also incorporated by reference herein.

Example 3

The third example arises when an insurance case worker refuses to approve proper care requests versus "available treatment" or other to stop/delay claim closure. For example, in a distal biceps rupture, if a patient fails to appear for an examination, or is delayed in confirmatory diagnostic testing (MRI scan) it can result in increased permanent impairment and functional limitations. When a requested diagnostic or therapeutic intervention is submitted and challenged by the carrier, a time period known as the "peer to peer call" takes place. If the treating provider misses the 'peer to peer' call, this can result in denial of treatment request. This leads to a situation of diminished "available treatment". The appeals process for a denial is similarly complex and time sensitive, meaning requests for independent medical review of a qualified medical examiner (state appointed second opinion examination event) must be coordinated. Again, in any of these "appeal processes" a misfiling or mistiming of an administrative event can result in stalemate of options.

Example 4

In the fourth example, the employer can be reluctant to send an injured worker for a medical evaluation due to:
  fear of increased insurance rate hikes
  they do not know the system and fail to understand proper insurance protocols
  believe the Worker is "faking"
  an attempt of "retaliation" for a human resource event
  not having a clear human resource policy to allow the work schedule to allow medical evaluations, therapy visit and administrative activities (depositions, insurance interviews etc.)

there can be a liability conflict due to the employer having changed insurance policies with neither carrier willing to assume responsibility the employer may simply have not purchased industrial injury insurance. In this case the worker is placed into the "Uninsured Employers Benefits Trust Fund" (UEBTF), which may or may not have funding for the year depending on the calendar year date of the injury Example 5

In the fifth example, the oversight board and state administrative remedies (the Qualified Medical Exam (QME) Process) are also sources of timing hiatus and process breakdown.

Judges frequently receive partially developed medical cases. The judge or oversight board sends these individuals back to their doctors or can require assignment of a new Primary Treating Physician (PTP). The role of the judge is to assure compliance to legislated guidelines, assuring the integrity of the process.

The Qualified Medical Examiners, as an example in California, are physicians who have passed a state administrative exam that verifies competency in the regulatory rules of impairment rating and repair. Because there is no clinical aspect to this certification, there is no demonstration of competency in the impairment rating process. Having the QME certification does not indicate clinical impairment rating competency.

The registry of QME doctors is regulated by the DWC and a lottery panel doctor is assigned to a case based on the geographic location of the Worker. The QME evaluator is not a primary treating doctor, and therefore, their findings and treatment recommendations are not mandates for the PTP to execute. Similarly, the QME recommendations are not prioritized above the Utilization Review (UR) process. A Utilization Review is a third party consultation process of other physicians and is a form of "Peer to Peer" review.

Even if the PTP chooses to adopt and recommend the QME treatment protocols, the insurance process still might not approve it. Further, the UR process could deny the recommendation based on evidence based guidelines. Either way, the QME recommendations remain simply this, recommendations. The QME could, however, find a Worker MMI and render an impairment exam and whole person impairment (WPI). Recall the QME is not proven competent with regards to impairment rating in the state exam, and therefore, their exams can have similar errors to that of any other medical provider in the system with regards to flaws in completeness, rigor and ARS interpretations.

As described above, there is a myriad of causes for the brake down of the IRP. This introduces an opportunity to improve the IRP.

SUMMARY OF THE INVENTION

The present invention enhances the execution of the telemedicine impairment repair process (IRP) from a work related incident to claim closure. The invention assists stakeholders by monitoring the claim process and reminding the stakeholders of stakeholder roles and responsibilities throughout the process. This maintains a prudent time frame for the reported injury and/or illness. A method of and system for executing an impairment repair process addresses flaws in the current process by implementing timing guided by legislation and best medical practices. Key aspects of the impairment repair process are addressed to ensure prudent timing and accuracy of claim development, claim monitoring, and initiating stakeholder communication to claim closure. The process is implemented in multiple stages including, assessment, documentation, prescribed treatment, and analysis of outcome. Assessment of Maximal Medical Improvement (MMI) is a critical element of claim closure as is the delivery of a complete data package including a report of the injury, therapy and a resulting impairment to the worker's compensation oversight authorities.

In one aspect, a method of executing an impairment repair process comprises recording a pre-employment injury status of a hired worker. After an injury event, a work related incident report is initiated, based upon the incident report, beginning a treatment plan, wherein the treatment plan creates a unique time frame for treatment and defines one or more stakeholder responsibilities within the treatment plan. Entering an impairment repair loop as defined by the treatment plan. Outputting an impairment rating, and exiting the impairment repair loop. In some embodiments, the method comprises recording a pre-employment injury status of a hired worker comprises screening the worker for pre-existing injuries. In some embodiments, the pre-employment injury status is stored in a HIPAA compliant database. The treatment plan enables a treating clinician to select one or more therapies for the injury. In some embodiments, the one or more therapies for the injury further define the time frame for treatment and the one or more stakeholder responsibilities within the treatment plan. The impairment repair loop comprises executing the one or more therapies and stakeholder responsibilities within the treatment plan. In some embodiments, a reminder is sent to the one or more stakeholders if a therapy is not executed according to the treatment plan. In some embodiments, outputting an impairment rating comprises determining a Maximal Medical Improvement. In some of these embodiments, the Maximal Medical Improvement depends on the pre-employment injury status of the hired worker. In some embodiments, exiting the impairment repair loop comprises delivering a data package to a worker's compensation oversight board.

In another aspect, a method of driving an impairment repair process comprises after an injury event, initiating a work related incident report, based upon the injury event, defining one or more treatment steps and stakeholder duties for resolution of the injury, inquiring to determine whether the one or more that one or more treatment steps and stakeholder duties have occurred, and if it is determined that the one or more treatment steps and stakeholder duties have not occurred, sending a reminder to the one or more stakeholders. In some embodiments, the incident report is uploaded to and stored in a HIPAA compliant database. In some embodiments, the treatment steps enable a treating clinician to select one or more therapies for the injury. In further embodiments, the one or more therapies for the injury further define the treatment steps and the stakeholder duties. In some embodiments, if a reminder is sent to the one or more stakeholders, the occurrence is logged.

In a further aspect, a system for executing an impairment repair process comprises a database comprising injury status of a worker, wherein the injury status of the worker is updated by one or more stakeholders, an execution engine in communication with the database, wherein the execution engine is configured to query the database as to the injury status of the worker based on a treatment plan, and wherein the execution engine sends a reminder to the one or more stakeholders if the treatment plan is not followed. In some embodiments, one or more pre-existing injuries of the worker are stored within the database. The database can comprise a HIPAA compliant database. In some embodiments, the treatment plan comprises one or more clinician recommended therapies for the injury. In some embodiments, a reminder is sent to the one or more stakeholders if a therapy is not executed according to the treatment plan. In some embodiments, if a reminder is sent to the one or more stakeholders it is logged within the database.

DETAILED DESCRIPTION OF THE EMBODIMENTS

Figure 1:
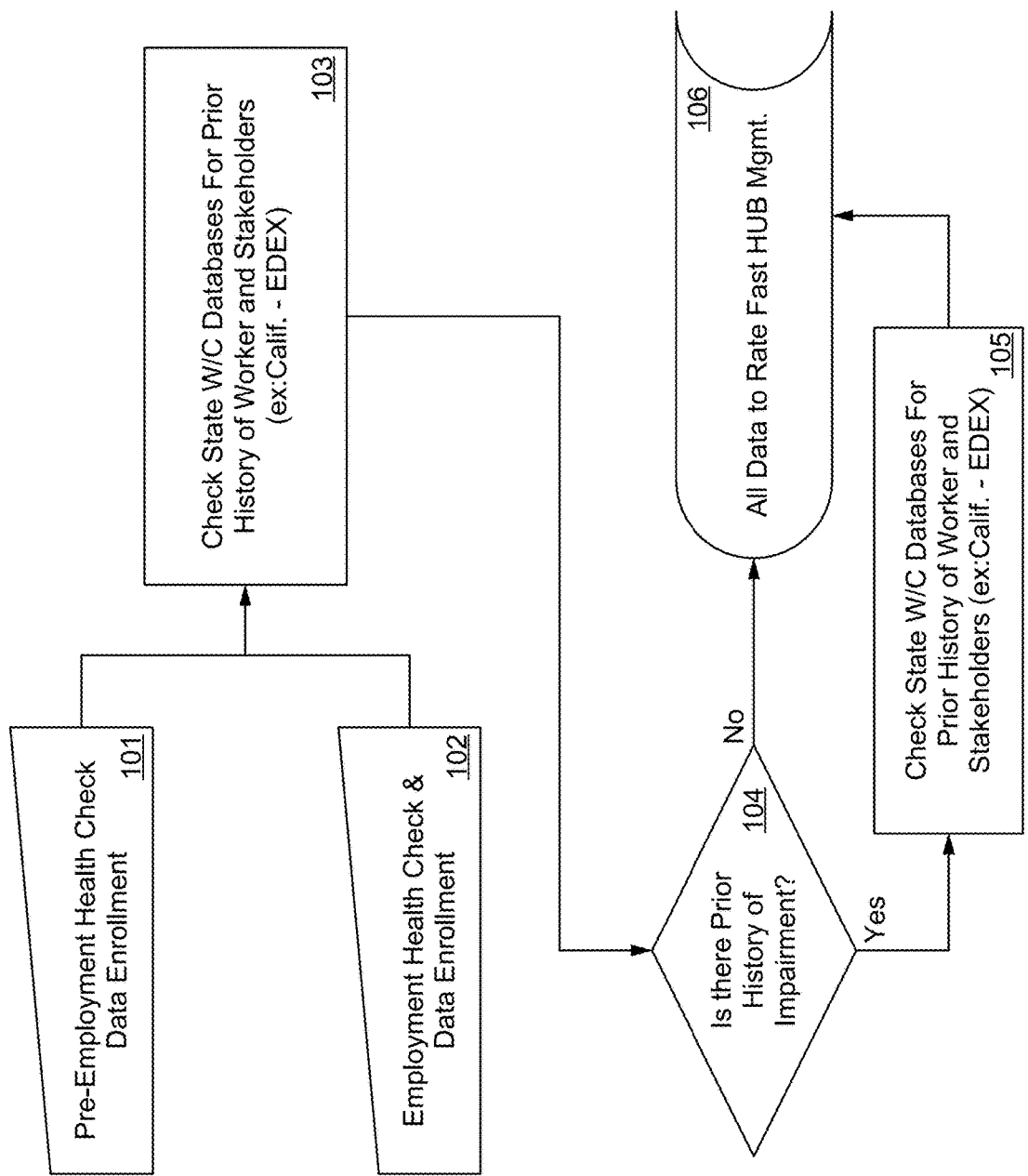
FIG. 1 illustrates a pre-employment recruitment process of a impairment repair process in accordance with some embodiments.

Embodiments of the invention are directed to a centralization of the Impairment Repair Process (IRP) driven by administrative rule sets (ARS's) derived and interpreted from the law to establish the timing of the various events and stages based on the specific injury and/or injuries present in the worker and how the injury (pathology) is responding to the therapies and treatments and communicate to each stakeholder their responsibilities within the IRP. The invention establishes a unique time frame for each of the events and stages of the IRP and then takes an active role of communicating and reminding each stakeholder of its role and responsibilities in the IRP. In this manner, the present invention leverages society-based value criteria to evaluate the completeness of and the level of impairment repair resulting in a prudent time frame unique to each worker injury case. The present invention prompts stakeholders to observe a discrete set of regulations and timetable. The invention becomes the transparent policeman of the IRP and brings accountability to the stakeholders in the delivery of the available treatment to driver the claim forward to that time at which a Maximal Medical Improvement (MMI) is determined.

Reference will now be made in detail to implementations of a method of and system for executing an impairment repair process as illustrated in the accompanying drawings. The same reference indicators will be used throughout the drawings and the following detailed description to refer to the same or like parts. In the interest of clarity, not all of the routine features of the implementations described herein are shown and described. It will be appreciated that in the development of any such actual implementation, numerous implementation-specific decisions can be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

As described below, the figures depict the IRP as contemplated by the present invention. The Figures and the IRP also incorporate one or more sub-processes and or ARS's such as described within the '067 Application. The purpose of the processes as described within the Figures is to address the current flaws within the IRP by putting into place a process of time and accountability for the stakeholders, such as physicians, injured workers, employers, insurance companies, nurses, case managers, medical equipment vendors, and others. In addition to a proactive communication algorithm driving the IRP, there is ongoing documentation of the timing, type, and specific communication and response or non-response from the various stakeholders.

As stated above, the process is defined by the legislation that governs the appropriate jurisdiction. The complete data package is delivered to the appropriate state oversight board, which enables that authority to take the appropriate action of or against the stakeholders in the process.

Referring now to FIG. 1, an initiation of the IRP process is shown therein. The process 100 begins with an initial recruitment and/or an enrollment procedure. As part of the enrollment procedure 100 a worker or recent hire undergoes a pre-employment health check 101. The data from the health check 101 is recorded as personal health information (PHI) and is stored within a HIPAA compliant database. For employees at the time this process is implemented as a health check and is performed in the step 102. In the step 103, state and other workers compensation databases are also searched for any prior cases that involved the worker. If, based on the search, it is found that the worker has a prior impairment 104, then an apportionment calculation for that injury can be done, if it is not already available in the step 105. The apportionment calculation can be done according to those as discussed within the '067 Application. The PHI of the worker, including any prior injuries and/or apportionment calculations for the prior injuries is stored within the HIPAA compliant database in the step 106. This database can also store historical data for the worker, doctors, employers and insurance companies.

Figure 2:
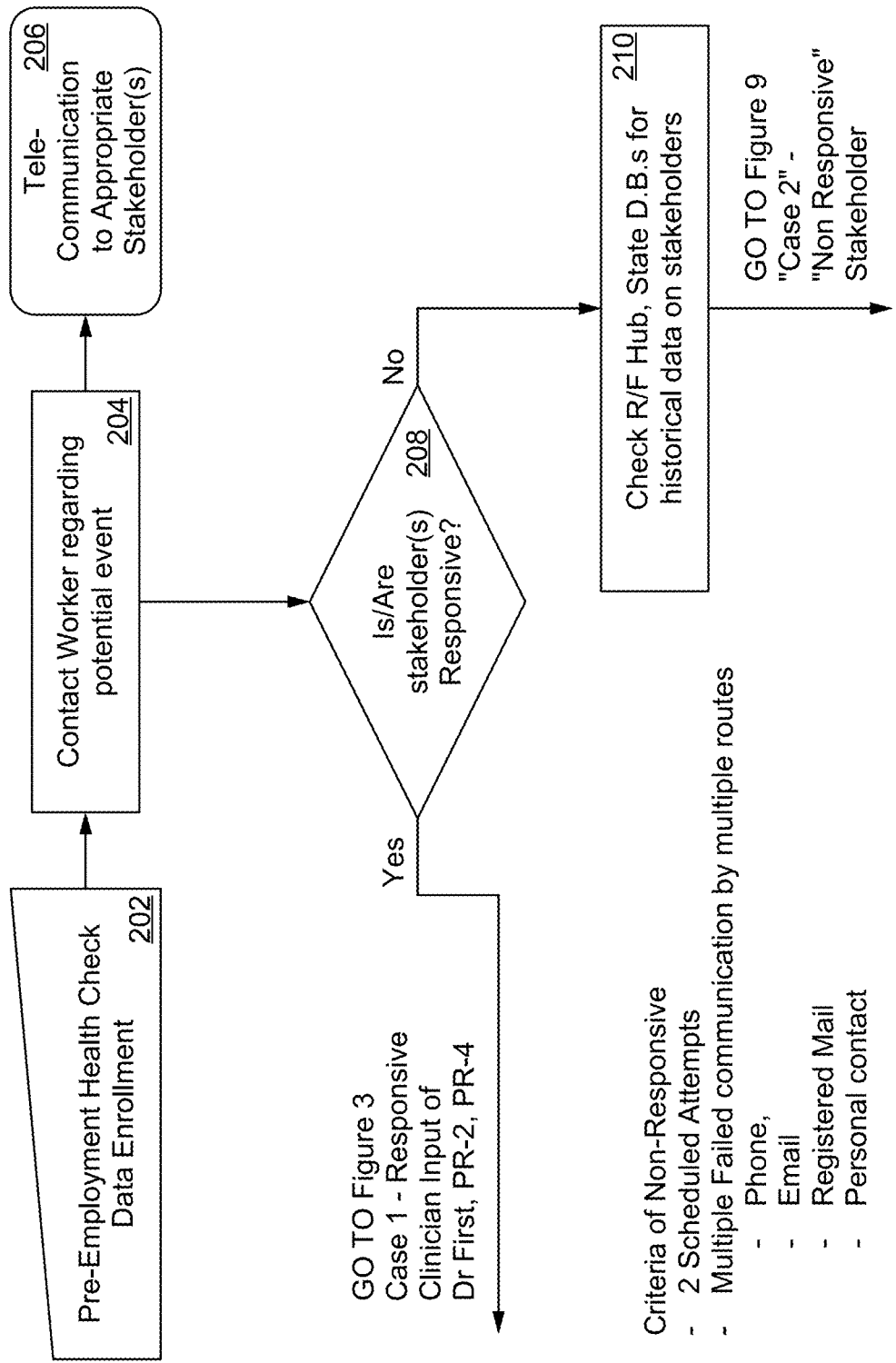
FIG. 2 illustrates a beginning of the impairment repair process, at which point a work related incident report is initiated in accordance with some embodiments.

FIG. 2 illustrates a method of initiating an initial event report for the IRP. The method begins after an injury event occurs, which can give rise to a worker's compensation claim. In the step 202, a suspected, but not yet confirmed event is entered into the system. In the step 204, the worker is contacted regarding the potential worker's compensation event and in the step 206, any other appropriate stakeholders are contacted. In the step 208, it is determined whether the stakeholders have been responsive. If the stakeholders are responsive, then IRP can continue with the injured worker visiting a stakeholder clinician and a "responsive case" scenario can begin, such as shown within FIG. 3. If the stakeholders do not respond the database is examined in the step 210 and the process continues, such as shown within FIG. 9.

Figure 9:
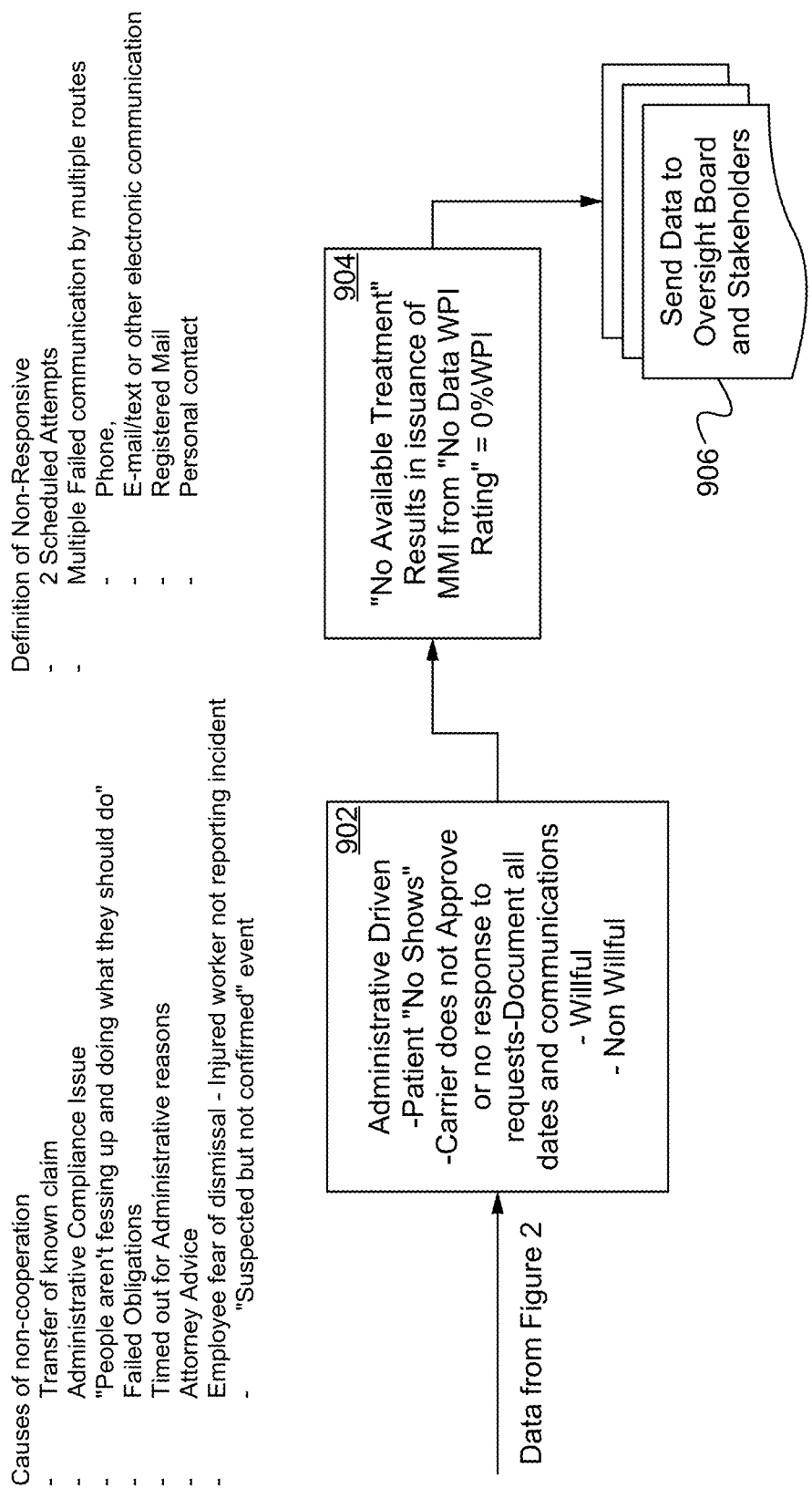
FIG. 9 illustrates possible situations in which one or more stakeholders are not responsive to the impairment repair process in accordance with some embodiments.

FIG. 9 illustrates possible situations in which one or more stakeholders are not responsive to the impairment repair process and the data to determine if the worker has sustained an injury does not exist. Consequently, an impairment rating cannot and is not determined. In the step 902, dates and communications to the stakeholder are documented. Then, in the step 904, the worker, with lack of data, is rated as having no impairment and given a 0% Whole Person Impairment ("0%" WPI). Further, the IRP also indicates that a MMI has been obtained. The non-responsive stakeholder has no data resulting in a rating of "no injury" and the assignment of "0%" WPI and MMI. The date and data set is documented, stored and then transmitted to the Oversight Review Board or Judge in the step 906.

If the stakeholders are not responsive throughout the process, then the system cannot determine an impairment rating and the IRP cannot obtain an MMI. Some common causes of non-responsiveness and/or non-cooperation, such as described above can include; transfer of a known claim, administrative compliance issues, stakeholders are not performing stated obligations, timing out of the process for administrative reasons, attorney advice, employee fear of dismissal leading to the injured worker not reporting the incident, and/or a "suspected but not confirmed" event. In this scenario, there is a recognition of willful and non-willful type of non-responsiveness. The documentation and communication methods and timing are different. However, the eventual data set sent to the oversight board or judge will contain the timing, method and content of the communications to enable the oversight entity to take appropriate actions.

Figure 3:
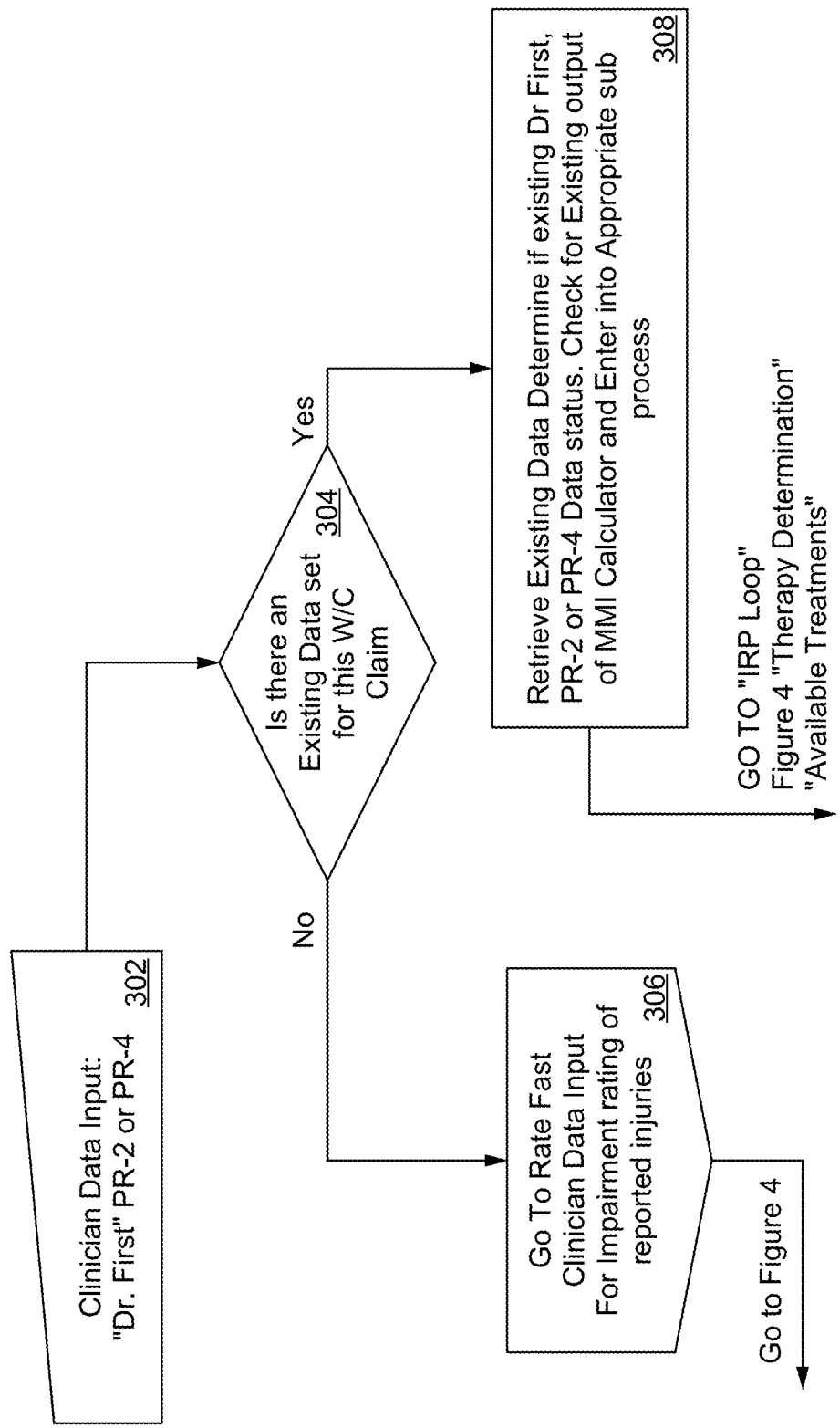
FIG. 3 illustrates a responsive case, in which the stakeholders, primarily the worker engage in the impairment repair process, in accordance with some embodiments.

FIG. 3 illustrates a "responsive case," in which the stakeholders, primarily the worker engage in the process. The clinician performs an assessment of worker status using guidance and clinical decision making based impairment rating algorithms. The data is entered in the step 302. In some instances, entry of the worker into the database, such as described above, discloses a prior existing report, such as indicated in the step 304. The system guides the physician from the rate fast impairment rating algorithms to an assessment of worker status. As described above, in some embodiments, as the worker is entered into the HIPAA compliant database, a prior report and/or injury is found. Based on the prior report, the physician is guided to the appropriate phase of the IRP depending upon the existing data set for the worker. If no data is found, then data is entered by the clinician in the step 306 and the process continues such as described within FIG. 4. If an existing data set is found in the step 304, then the data set is retrieved in the step 308 and process continues as described within FIG. 4.

Figure 4:
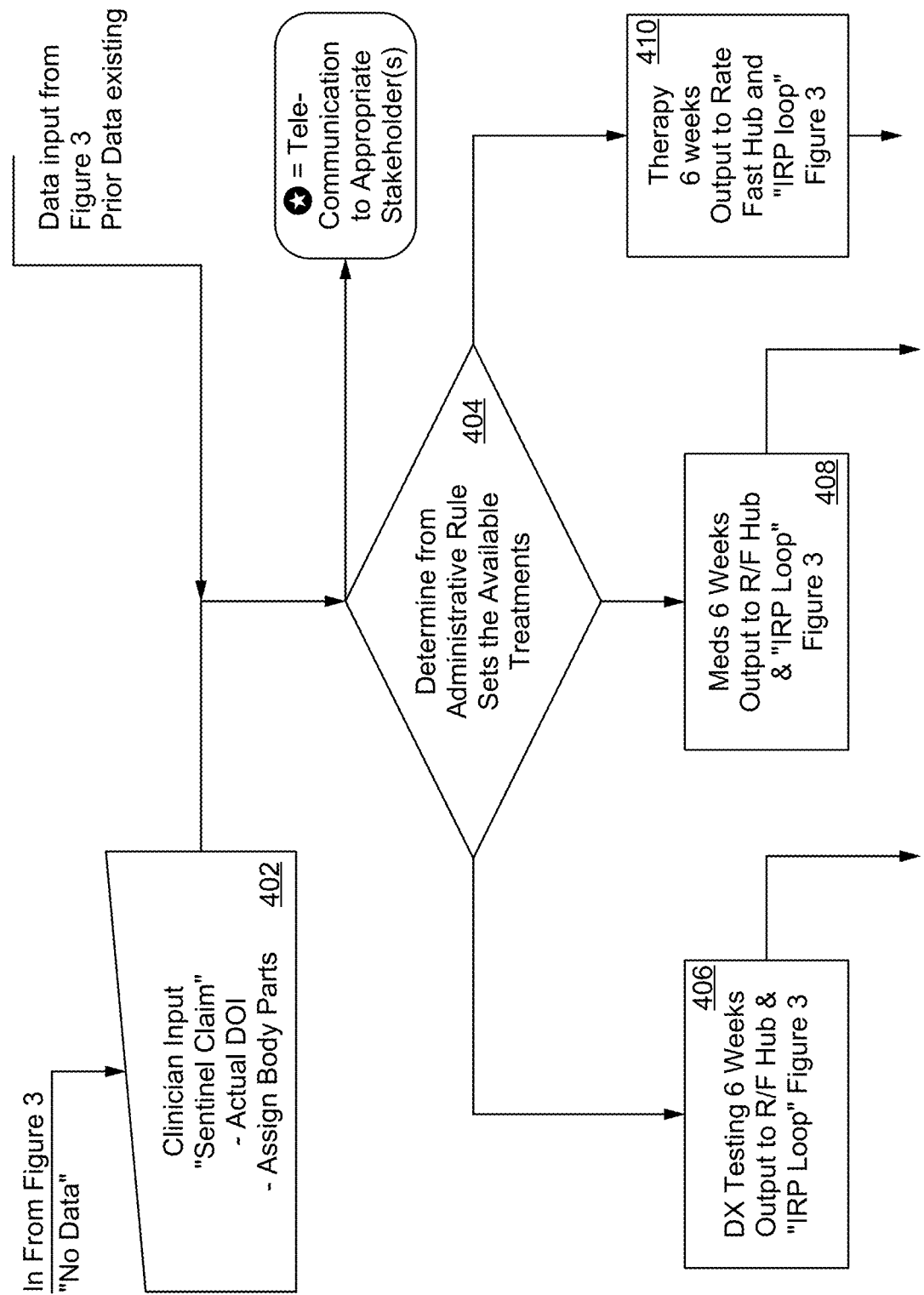
FIG. 4 illustrates a determination of appropriate therapies for an injured worker based on the phase of the impairment repair process in accordance with some embodiments.

The phase of the worker within the IRP guides the physician to an appropriate selection of therapies for the injured worker. FIG. 4 illustrates a determination of appropriate therapies for the worker based on the phase of the IRP. At this time, one or more timing clocks are initiated for the IRP as derived from the ARS s as described within the '067 Application. The one or more timing clocks are designed to guide the remainder of the IRP and are linked through legislative guidance, type of injury, and/or pathologies of the injured worker. The timing intervals eliminate the errors that might otherwise occur during the IRP. As shown within FIG. 4, the timing intervals are an example of a typical time frame and are not meant to limit a duration of a therapy time loop. As described above, if an existing data set is not found then one or more body parts are assigned and an original claim begins in the step 402. Then, in the step 404, based on the injury and the ARS s for the injury, available treatments are determined. In the steps 406-408, testing schedules, necessary medications and therapy schedules are uploaded to the database and the injured worker enters the impairment repair loop.

Figure 5:
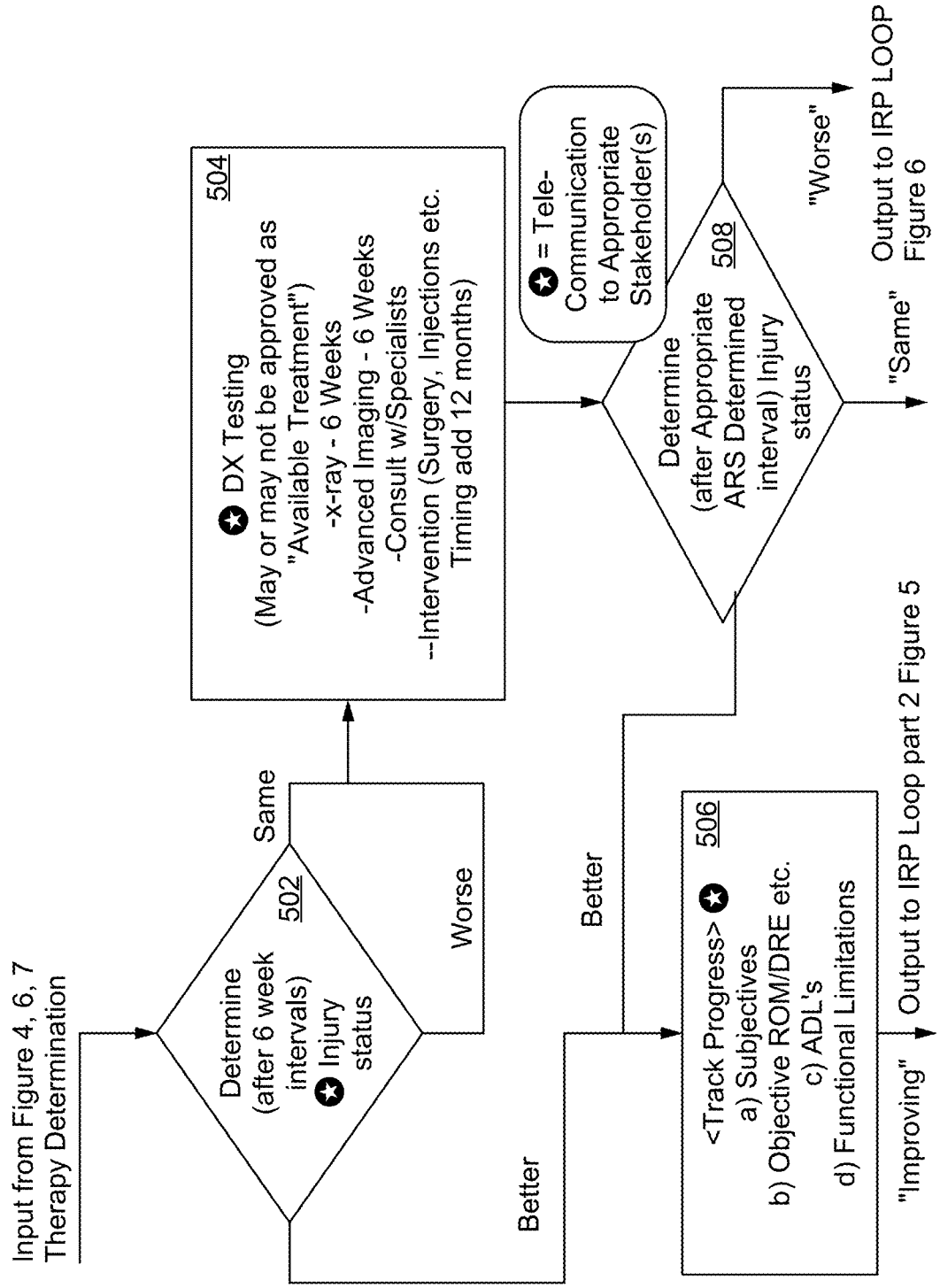
FIGS. 5-7 illustrate the impairment repair loop of the impairment repair process in accordance with some embodiments.
Figure 6:
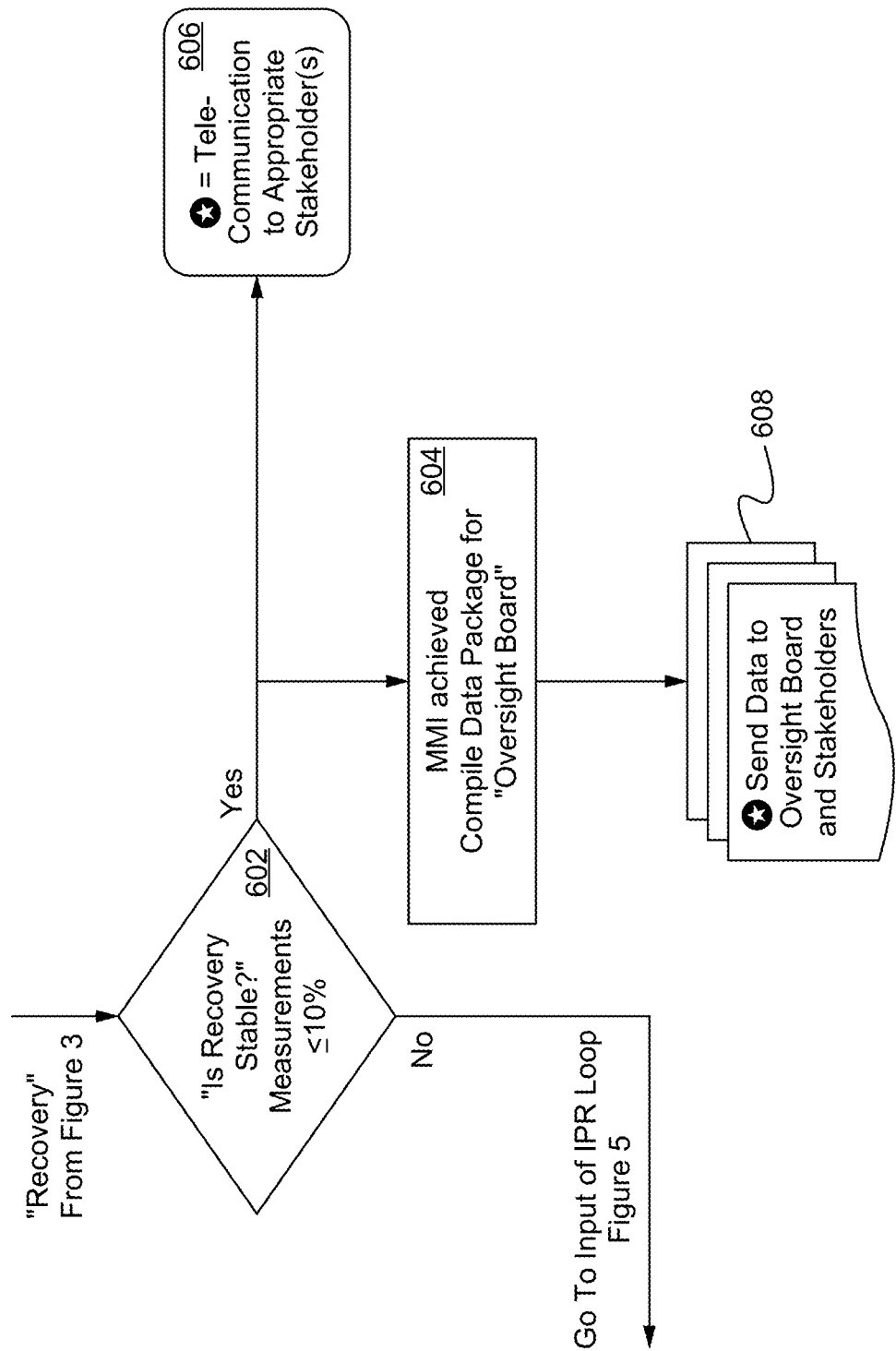
Figure 7:
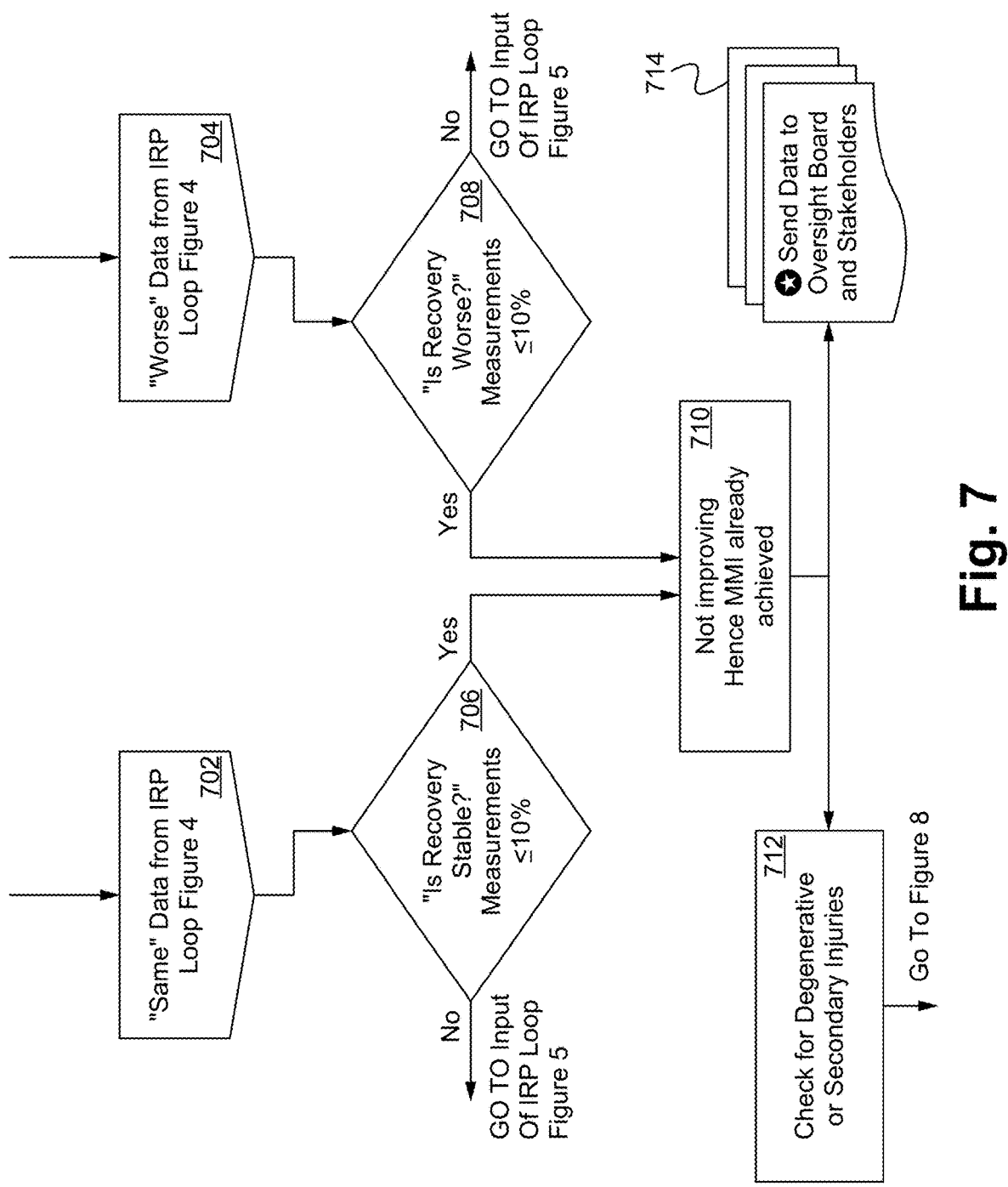

FIGS. 5-7 illustrate the impairment repair loop as the system maintains the reporting, communication and documentation activities. Principle to the reporting, communication and documentation activities is the telemedicine communication to the stakeholders as to the obligations throughout the process. Such obligations can include, but are not limited to informing an injured worker of therapy appointments, reminding the insurance case officer to review and approve therapies, and updating the communication to the employer as to the status of the injured worker.

FIG. 5 illustrates a possible first phase of the impairment repair loop. As shown within FIG. 5, in the step 502, an injury status can be determined at intervals as guided by the ARS and the treatment schedule. If at the step 502, it is determined that the injured worker is getting better then the worker's progress is logged in the step 506 and the worker continues to the second phase of the impairment repair loop, such as shown within FIG. 6. If however, in the step 502, it is determined that the injured worker is getting worse or the injury remains the same, then additional tests and/or treatments can be ordered in the step 504 and the injury status can be determined in the step 508 before the worker continues to the second phase of the impairment repair loop. The injury status of the injured worker as well as the continued treatment can be determined according to the relevant ARS determined interval.

FIGS. 6 and 7 illustrate potential exits of the impairment repair loop. As shown within FIG. 6, in the step 602, it is determined whether the recovery of the injured worker is stable. In some embodiments, recovery is stable when the injury measurements are within 10%. If in the step 602, it is determined that recovery is not stable, then the impairment repair loop and therapy continues, such as described within FIG. 4. If however, in the step 602 it is determined that recovery is stable then a data package is compiled for the oversight board in the step 604 and a message is sent to one or more stakeholders in the step 606. The data package is transmitted to the oversight board and the one or more stakeholders in the step 608.

In some embodiments, once a worker has achieved MMI, the data package is delivered to an appropriate oversight board, thus signaling the exit of the injured worker. For example, in California, such as described above, the package is delivered to the DWC Judge handling the case. Different exit points throughout the IRP are determined according to the system's determination of MMI, patient response and improvement from the initial injury and/or pathology.

FIG. 7 illustrates a potential exit of the impairment repair loop where it has been determined after further treatment that the injured workers condition is the same or has gotten worse.

If after further treatment such as described in relation to FIG. 4, it is determined that the condition of the worker remains the same in the step 702, then in the step 706, it is determined whether the recovery of the injured worker is stable. In some embodiments, recovery is stable when the injury measurements are within 10%. If in the step 706, it is determined that the injured worker is not stable, then the impairment repair loop and therapy continues, such as described within FIG. 5. If in the step 706, it is determined that recovery is stable, then in the step 710 it is verified that MMI has been achieved and a data package is sent to the oversight board and the one or more stakeholders in the step 714. After it is verified that MMI has been achieved, but the condition of the injured worker remains the same then the injured worker is checked for secondary injuries in the step 712 and treatment and analysis continues such as described within FIG. 8.

Similarly, if after further treatment such as described in relation to FIG. 4, it is determined that the condition of the worker is worse in the step 704, then in the step 708, it is determined whether the recovery of the injured worker is stable. In some embodiments, recovery is stable when the injury measurements are within 10%. If in the step 708, it is determined that the injured worker is not stable, then the impairment repair loop and therapy continues, such as described within FIG. 5. If in the step 708, it is determined that recovery is stable, then in the step 710 it is verified that MMI has been achieved and a data package is sent to the oversight board and the one or more stakeholders in the step 714. After it is verified that MMI has been achieved, but the condition of the injured worker remains the same then the injured worker is checked for secondary injuries in the step 712 and treatment and analysis continues such as described within FIG. 8.

Figure 8:
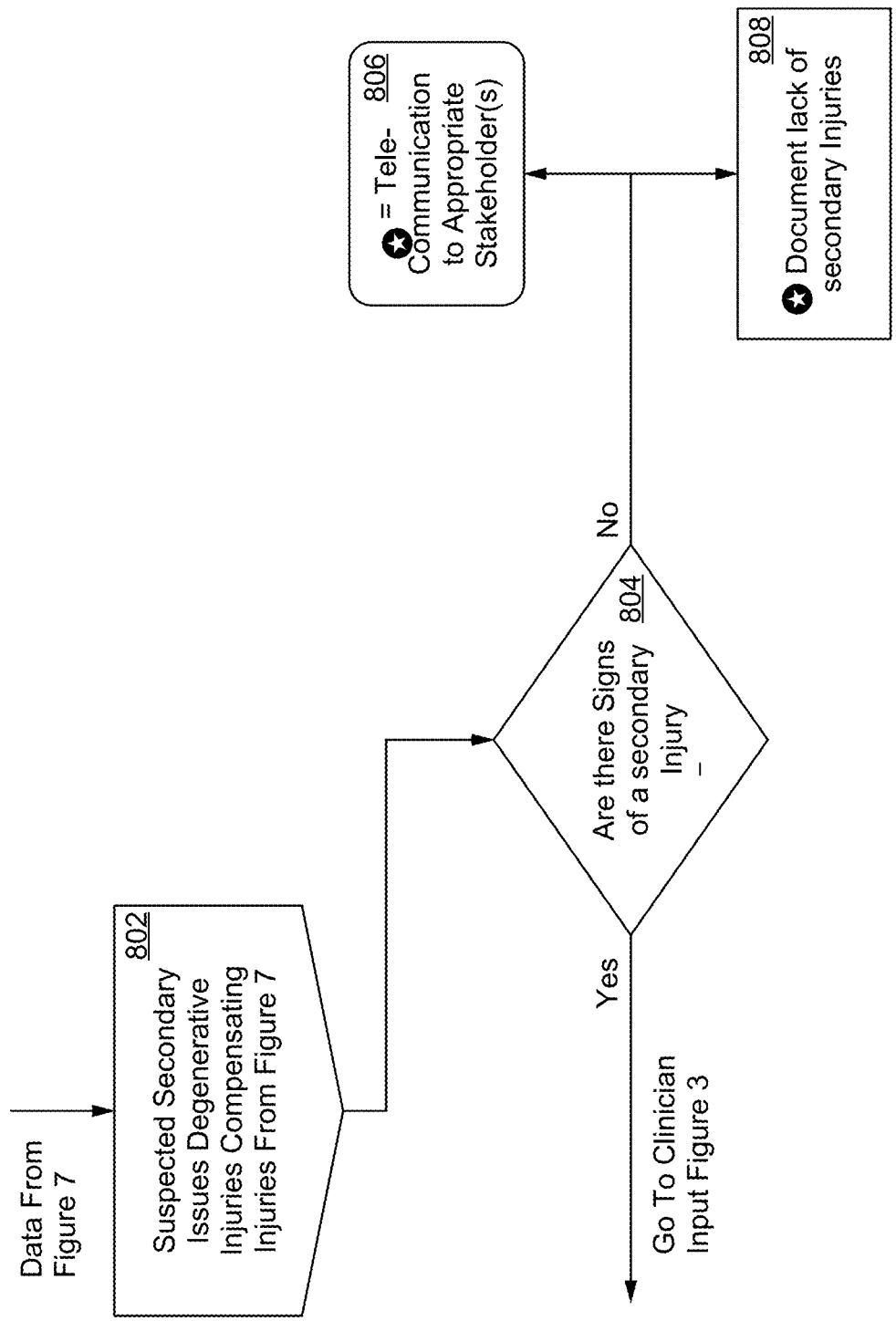
FIG. 8 illustrating requesting the analysis of the injured party for symptoms of a secondary injury that is possibly caused by the initial injury in accordance with some embodiments.

FIG. 8 illustrates a process employed by the system in which the injured party is screened for symptoms of a secondary injury that is possibly caused by the initial injury. This can occur, such as described within FIG. 7, when the injured worker has achieved MMI, but the worker's condition remains the same or has gotten worse. Such secondary injuries are often compensating or compensatory injuries that happen as adjacent body parts react to an increased strain or burden arising from the inability to use or to support the injured body part. For example, a left knee injury can cause a transfer of weight bearing and altered gait mechanics to the right uninjured knee, which subsequently becomes symptomatic.

In the step 802, the injured worker is examined for one or more suspected secondary and/or compensating injuries. If, in the step 804 it is determined that there are signs of a secondary injury, then the injured worker is further assessed such as shown within FIG. 3, regarding the new injury. If however, in the step 804 it is determined that there are not signs of a secondary injury, then a message is sent to one or more stakeholders in the step 806, and the lack of secondary injuries is documented in the step 808.

Figure 10:
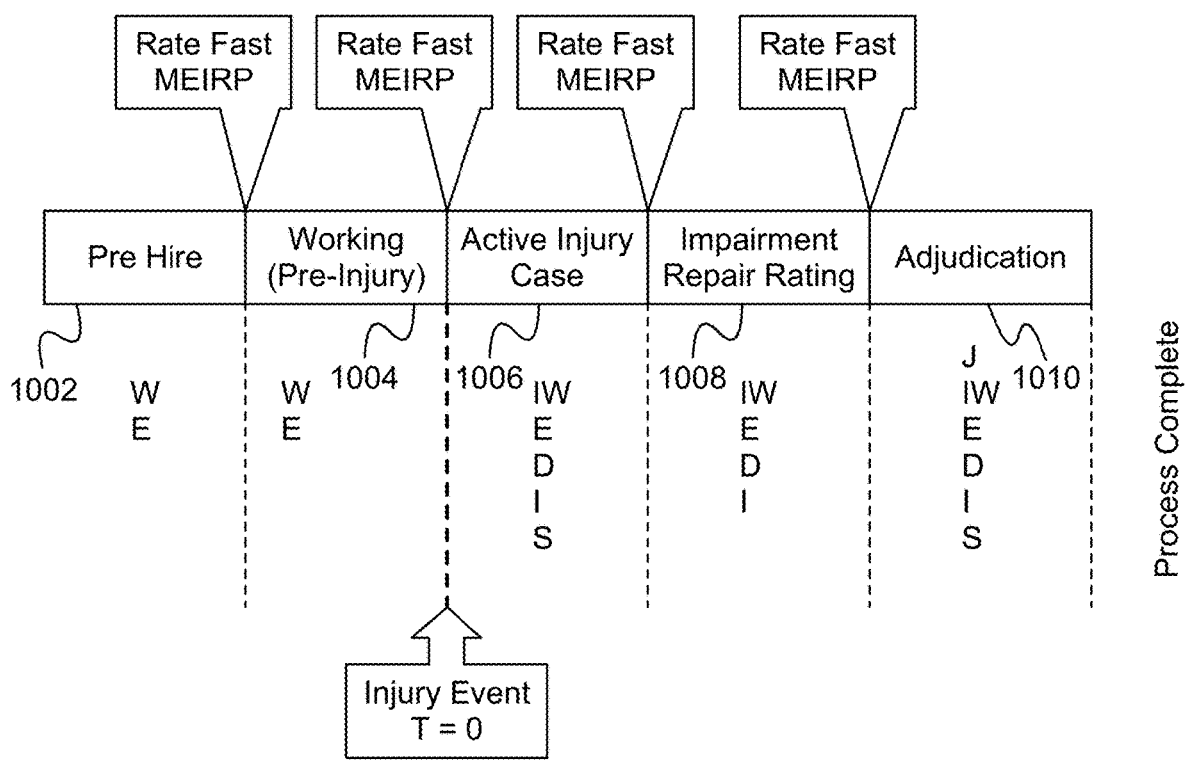
FIG. 10 illustrates a stakeholder map for the executing the impairment repair process in accordance with some embodiments.

FIG. 10 illustrates a stakeholder map for the executing the IRP, such as described above. As shown within FIG. 10, the role of each stakeholder, the worker or injured worker, the employer, the treating clinician or doctor, the insurance company or adjuster, the state, and the applicable review board are shown throughout the IRP. As shown within FIG. 10, the impairment repair process begins before the worker is hired 1002, at which time a pre-employment injury screening, such as described within FIG. 1 occurs. The worker begin working, pre-injury 1004. After an injury event occurs (T=0) 1006, the case is active and roles for the stakeholders, such as the injured worker, the treating clinician or doctor, the insurance company or adjuster, and the state are defined. The injured worker is treated according to a treatment plan and an impairment impair rating such as a MMI, for the injured worker is determined 1008. As described above, when the worker has achieved MMI, a data package is delivered to an appropriate oversight board, thus signaling the exit of the injured worker from the IRP 1010.

Figure 11:
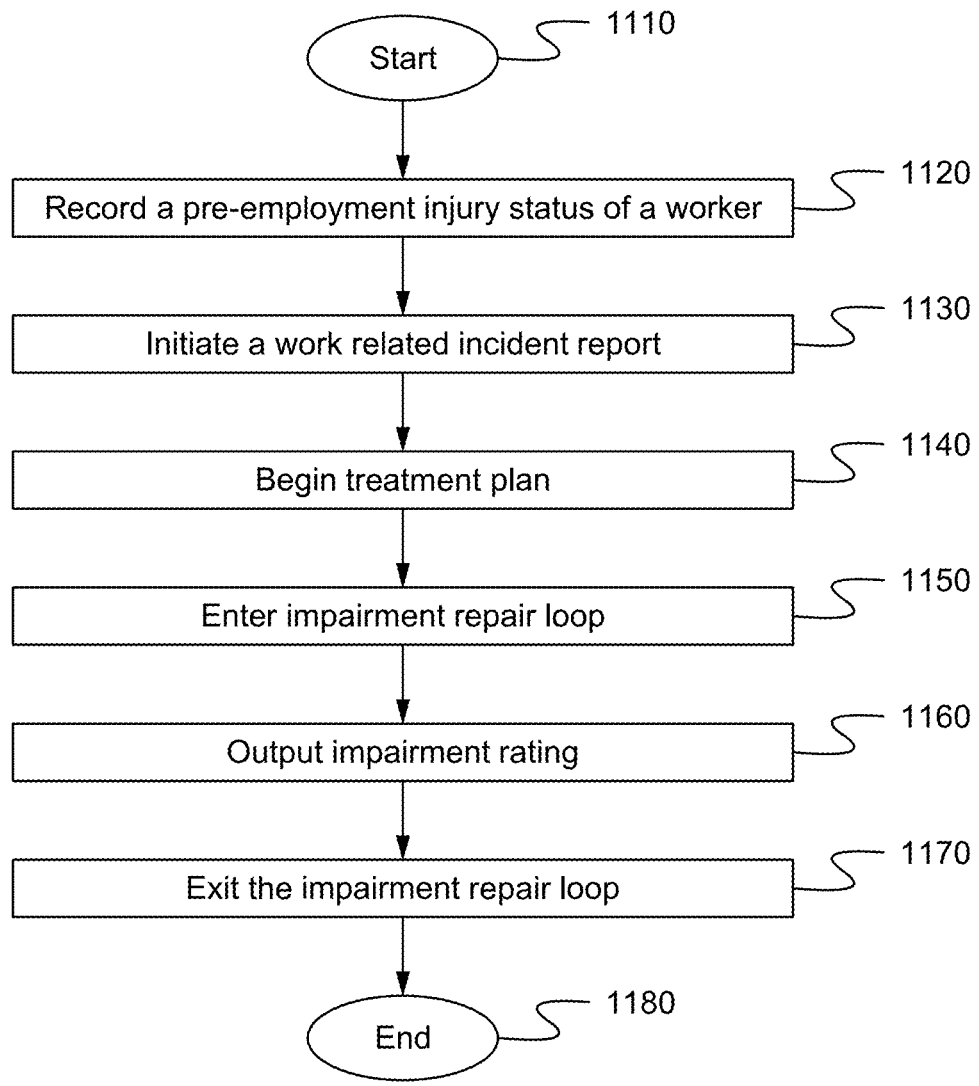
FIG. 11 illustrates a method of executing an impairment repair process in accordance with some embodiments.

FIG. 11 illustrates a method of executing an IRP, such as described above, in accordance with some embodiments. The method begins in the step 1110. In the step 1120, a pre-employment injury status of a hired worker is recorded. In some embodiments, this includes screening the worker for pre-existing injuries and impairment due to those injuries. The pre-employment injury status of the worker is stored in a HIPAA compliant database. In the step 1130, after an injury event occurs, a work related incident report is initiated. Based on the injury incident, the injured worker begins a treatment plan in the step 1140. In some embodiments, the treatment plan is defined by a unique time frame ad defines one or more stakeholder roles within the treatment plan. For example, in some embodiments, an outline of the treatment plan is defined by jurisdictional legislation and/or an appropriate state oversight board. The treatment plan and the stakeholder responsibilities within the treatment plan drive the injured worker toward treatment at which time a MMI can be determined.

In the step 1150, the injured worker enters an impairment repair loop as defined by the treatment plan. In some embodiments, the treatment plan enables a treating clinician to select one or more therapies for treatment of the injury. The one or more therapies can further define the time frame for treatment and the one or more stakeholder responsibilities within the treatment plan. In some embodiments, a reminder is sent to one or more of the stakeholders if a therapy is not approved and/or executed according to the treatment plan. In the step 1160, based on the treatment, an impairment rating is output. As described above, in some embodiments, a MMI is determined. In some embodiments, the MMI is determined according to one or more pre-existing injuries of the injured worker. In the step 1170, the injured worker exits the impairment repair loop. In some embodiments, exiting the impairment repair loop comprises delivering an appropriate data package to an appropriate worker's compensation oversight board. The method ends in the step 1180.

Figure 12:
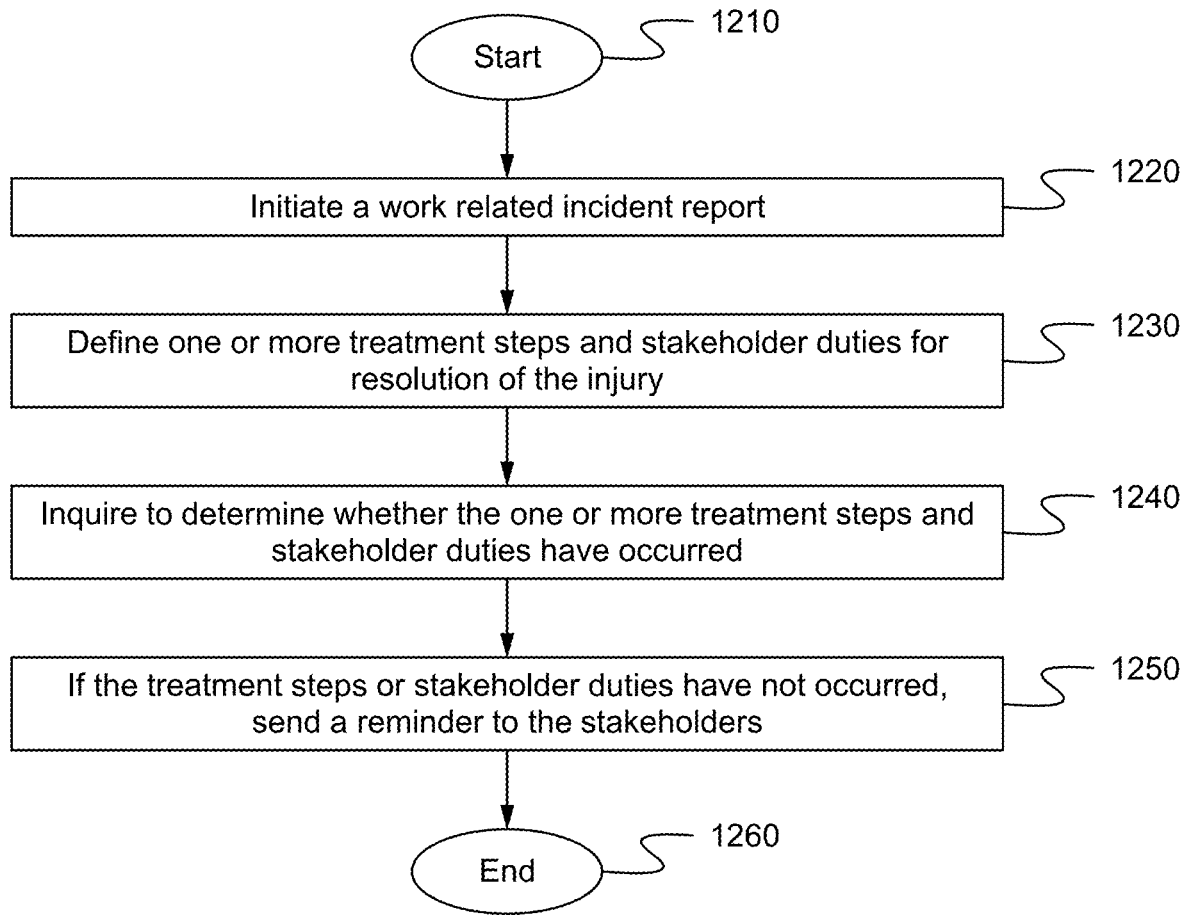
FIG. 12 illustrates a method of driving an impairment repair process in accordance with some embodiments.

FIG. 12 illustrates a method of driving an IRP, such as that described within FIG. 11. The method begins in the step 1210. In the step 1220, a work-related injury report is initiated. In some embodiments, the incident report is stored in a HIPAA compliant database. As described above, in relation to FIG. 11, based on the injury incident, the injured worker begins a treatment plan. In some embodiments, the treatment plan is defined by a unique time frame ad defines one or more stakeholder roles within the treatment plan. For example, in some embodiments, an outline of the treatment plan is defined by jurisdictional legislation and/or an appropriate state oversight board. The treatment plan and the stakeholder responsibilities within the treatment plan drive the injured worker toward treatment at which time a MMI can be determined.

In some embodiments, after each step of treatment, the responsible stakeholder logs the action in the HIPAA compliant database. For example, the treating clinician can log therapy treatments in the database after the treatment occurs. Additionally, the insurance adjuster can log into the database to approve necessary treatments and log that the treatment was approved.

In the step 1240, the database and/or treatment log is queried to determine whether one or more treatment steps and stakeholder duties have occurred. For example, in some embodiments, it is queried to determine that the injured worker has been attending the necessary treatments. Alternatively, or in conjunction, it can be queried to determine whether the insurance adjuster has approved any outstanding treatments. If, based on the query, it is determined that the responsible stakeholder has not performed an outstanding duty, then, in the step 1250 a reminder is sent to the one or more responsible stakeholders. In some embodiments, when a reminder is sent to the one or more stakeholders, the occurrence is logged. In some embodiments, the treatment plan and the one or more stakeholder duties are stored within the database such that a reminder can be automatically sent to a stakeholder if an action is missed. The method ends in the step 1260.

Figure 13:
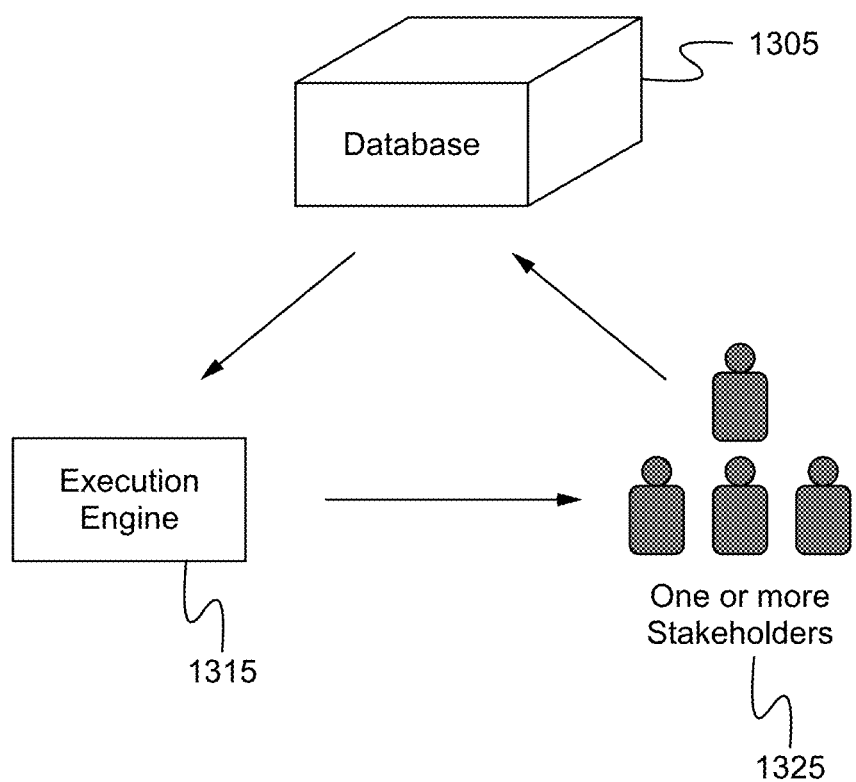
FIG. 13 illustrates a system for executing an impairment repair process in accordance with some embodiments.

FIG. 13 illustrates a system for executing an impairment repair process. The system 1300 comprises a database 1305, which stores an injury status of one or more workers. In some embodiments, the database 1305 comprises a HIPAA compliant database. In some embodiments, the database stores a pre-employment injury status of the one or more workers. The database is able to be updated when a work related incident occurs. As shown within FIG. 13, the database is in communication with an execution engine 1315, which is implemented on a computing device. In an embodiment, programmed instructions that are programmed to execute the functions described herein are referred to as the execution engine 1315. The execution engine 1315 is configured to query the database as to the injury status of the one or more workers based on a treatment plan and send a reminder to one or more stakeholders 1325 if the treatment plan is not followed. In some embodiments, the treatment plan comprises one or more clinician recommended therapies for the injury. In some embodiments, after a reminder is sent to the one or more stakeholders, it is logged within the database. In some embodiments, the treatment plan is defined by a unique time frame and defines one or more stakeholder roles within the treatment plan. For example, in some embodiments, an outline of the treatment plan is defined by jurisdictional legislation and/or an appropriate state oversight board. As described above, the treatment plan and the stakeholder responsibilities within the treatment plan drive the injured worker toward treatment at which time a MMI can be determined.

In operation, the method of and system for executing an impairment repair process such as described above addresses flaws in the current process by implementing timing guided by legislation and best medical practice. Key aspects of the impairment repair process are addressed to ensure prudent timing by assuring accuracy of claim development, monitoring, and initiating communication to closure. The process is implemented in multiple stages including, assessment, documentation, prescribed treatment, and analysis of outcome.

The medical processes and therapies are augmented in appointment timing, ordering of treatment, and evaluating the results in a timely fashion. The presence of a central communication within the telemedicine process provides a critical service to inform stakeholders how to appropriately respond to administrative benchmarks and variations and/or deviations within the case process.

Additionally, after exiting the impairment repair process, the injured worker has a packaged impairment rating along with a case history that the worker can take before a judge much sooner and with more information for final adjudication. Consequently, the claim process is streamlined thus enabling an injured worker to receive therapy and return to normal life activities sooner.

Further, an employer can take appropriate actions in a more timely manner due to the ongoing communications and status reports from the HIPAA compliant database and execution engine. In the event of permanent impairment impacting the worker's job function (as determined by an appropriate oversight board), the employer can more quickly determine a reasonable accommodation and/or release the injured employee without excess payroll and/or benefits cost.

Moreover, the development of a case history within the database enables more precise pricing estimates and the added infrastructure drives the process, which enables a more consistent outcome for all stakeholders. The ability of stakeholders to have an estimate of time and potential impairment repair cost allows the stakeholders to make appropriate plans. As such the method of and system for executing an impairment repair process such as described above has many advantages.

The present invention has been described in terms of specific embodiments incorporating details to facilitate the understanding of the principles of construction and operation of the invention. As such, references, herein, to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. A method of establishing a unique time frame for one or more stages of execution within an impairment repair process and reducing errors occurring during the impairment repair process, the method comprising:

storing, by a server computer, a pre-employment injury status of a hired worker in a HIPAA compliant database;

after an injury event, initiating a work related incident report for an injury associated with the injury event;

based upon the incident report, defining, by the server computer, a treatment plan that includes a time frame for treatment and intervals for checkups, wherein the treatment plan defines one or more therapies and one or more stakeholder responsibilities, wherein the time frame and intervals are determined according to at least one administrative rule set;

entering an impairment repair loop as defined by the treatment plan, wherein during the impairment repair loop:

the one or more therapies defined by the treatment plan are executed;

the one or more stakeholder responsibilities defined by the treatment plan are executed;

a reminder is automatically sent to one or more stakeholders if the treatment plan is not followed, wherein the reminder sent to the one or more stakeholders is logged;

a condition of the hired worker is obtained at an interval of the intervals, wherein the condition of the hired worker is one of improving, worsening, or is stable; and an impairment rating is output, wherein the impairment rating is determined by:

receiving, by the server computer from a client computer, encrypted data including a digital clinical data set that includes an observed data set and completed therapies for the injury, wherein the observed data set is obtained from one or more tests performed by a treating clinician on the hired worker, wherein the clinical data set is encrypted by a shell program executing on the client computer and transmitted to the server computer by the shell program to improve computing performance at the server computer, wherein the shell program controls a graphical user interface guiding the treating clinician through data collection and entry process by:
  generating at least
    a pictorial prompt of a map for identifying an employer location and a treatment location,
    a selection menu to enable identification of at least one body part for the injury, and
    entry fields to enable input of the observed data set and the completed therapies for the injury,
  receiving the employer location, the treatment location, the at least one body part for the injury, the observed data set and the completed therapies for the injury via the pictorial prompt of the map, the selection menu, and the entry fields;
  selecting the at least one administrative rule set from a plurality of administrative rule sets based on the employer location and the treatment location;
  based on the at least one administrative rule set, performing real-time validation calculations of the observed data set as the observed data set is being entered and alerting the treating clinician when the real-time validation calculations indicate that entered input data is outside expected data ranges for the injury;
  decrypting the encrypted data to obtain the clinical data set;
  selecting, based on the injury, a particular impairment calculator from a plurality of impairment calculators; and
  importing data from the clinical data set into one or more fields of the particular impairment calculator, wherein the particular impairment calculator applies a plurality of criteria for the injury, as defined by the at least one administrative rule sets, to determine an impairment value, wherein the impairment rating for the injury is based on the impairment value;
exiting the impairment repair loop when the condition of the hired worker is not improving, wherein exiting the impairment repair loop comprises generating a data package that includes data relating to the one or more therapies and the impairment rating; and
transmitting the data package to a destination.

2. The method of claim 1, further comprising obtaining the pre-employment injury status of the hired worker by screening the hired worker for pre-existing injuries.

3. The method of claim 1, further comprising storing the work related incident report in the HIPAA compliant database.

4. The method of claim 1, wherein the treatment plan enables the treating clinician to select the one or more therapies for the injury associated with the injury event.

5. The method of claim 4, wherein the one or more therapies for the injury further define the time frame for treatment and the one or more stakeholder responsibilities within the treatment plan.

6. The method of claim 1, wherein outputting the impairment rating comprises determining a Maximal Medical Improvement.

7. The method of claim 6, wherein the Maximal Medical Improvement depends on the pre-employment injury status of the hired worker.

8. The method of claim 1, wherein the data package is transmitted to a workers compensation oversight board.

9. A computer-implemented method of establishing a unique time frame for driving an impairment repair process and reducing errors occurring during the impairment repair process, the method comprising:
  initiating a work related incident report for an injury sustained by an injured worker;
  based upon the injury event, determining, by a server computer, a treatment plan that includes a time frame for treatment and intervals for checkups according to at least one set of administrative rule set, the treatment plan defining one or more therapies and one or more stakeholder duties;
  inquiring to determine whether the treatment plan has been followed;
  based on a determination that the treatment plan is not followed, automatically sending a reminder to one or more stakeholders, wherein the reminder sent to the one or more stakeholders is logged;
  obtaining a condition of the injured worker at an interval of the intervals, wherein the condition of the injured worker is one of improving, worsening, or is stable;
  outputting an impairment rating, comprising:
    receiving, by the server computer from a client computer, encrypted data including a digital clinical data set that includes an observed data set and completed therapies for the injury, wherein the observed data set is obtained from one or more tests performed by a treating clinician on the hired worker, wherein the clinical data set is encrypted by a shell program executing on the client computer and transmitted to the server computer by the shell program to improve computing performance at the server computer, wherein the shell program controls a graphical user interface guiding the treating clinician through data collection and entry process by:
      generating at least
        a pictorial prompt of a map for identifying an employer location and a treatment location,
        a selection menu to enable identification of at least one body part for the injury, and
        entry fields to enable input of the observed data set and the completed therapies for the injury,
      receiving the employer location, the treatment location, the at least one body part for the injury, the observed data set and the completed therapies for the injury via the pictorial prompt of the map, the selection menu, and the entry fields;
    selecting the at least one administrative rule set from a plurality of administrative rule sets based on the employer location and the treatment location;
    based on the at least one administrative rule set, performing real-time validation calculations of the observed data set as the observed data set is being entered and alerting the treating clinician when the real-time validation calculations indicate that entered input data is outside expected data ranges for the injury;
    decrypting the encrypted data to obtain the clinical data set;
    selecting, based on the injury, a particular impairment calculator from a plurality of impairment calculators; and importing data from the clinical data set into one or more fields of the particular impairment calculator, wherein the particular impairment calculator applies a plurality of criteria for the injury, as defined by the at least one administrative rule set, to determine an impairment value, wherein the impairment rating for the injury is based on the impairment value;

generating a data package that includes data relating to the impairment rating; and transmitting the data package to a destination.

10. The method of claim 9, wherein the incident report is uploaded to and stored in a HIPAA compliant database.

11. The method of claim 9, wherein the treatment plan enables the treating clinician to select the one or more therapies for the injury associated with the injury event.

12. The method of claim 11, wherein the one or more therapies for the injury further define the time frame for treatment and the one or more stakeholder duties within the treatment plan.

13. A computer-implemented system for establishing a unique time frame for executing an impairment repair process and reducing errors occurring during the impairment repair process, the system comprising:

a database comprising treatment plans and injury statuses of workers, wherein the injury statuses of the workers are updated by one or more stakeholders; and a server computer in communication with the database, wherein the server computer comprises instructions stored in a storage media and which, when executed by the server computer, cause the server computer to perform:

querying the database for an injury status of the a worker;

sending a reminder to the one or more stakeholders if a treatment plan for the worker is not followed, wherein the reminder sent to the one or more stakeholders is logged within the database;

obtaining a condition of the worker at an interval defined by the treatment plan for the worker, wherein the condition of the hired worker is one of improving, worsening, or is stable;

outputting an impairment rating based on the condition, comprising:

receiving, by the server computer from a client computer, encrypted data including a digital clinical data set that includes an observed data set and completed therapies for the injury, wherein the observed data set is obtained from one or more tests performed by a treating clinician on the hired worker, wherein the clinical data set is encrypted by a shell program executing on the client computer and transmitted to the server computer by the shell program to improve computing performance at the server computer, wherein the shell program controls a graphical user interface guiding the treating clinician through data collection and entry process by:

generating at least
a pictorial prompt of a map for identifying an employer location and a treatment location,
a selection menu to enable identification of at least one body part for the injury, and
entry fields to enable input of the observed data set and the completed therapies for the injury, receiving the employer location, the treatment location, the at least one body part for the injury, the observed data set and the completed therapies for the injury via the pictorial prompt of the map, the selection menu, and the entry fields;

selecting the at least one administrative rule set from a plurality of administrative rule sets based on the employer location and the treatment location;

based on the at least one administrative rule set, performing real-time validation calculations of the observed data set as the observed data set is being entered and alerting the treating clinician when the real-time validation calculations indicate that entered input data is outside expected data ranges for the injury;

decrypting the encrypted data to obtain the clinical data set;

selecting, based on the injury, a particular impairment calculator from a plurality of impairment calculators; and importing data from the observed data set into one or more fields of the particular impairment calculator, wherein the particular impairment calculator applies a plurality of criteria for the injury, as defined by the at least one administrative rule sets, to determine an impairment value, wherein the impairment rating for the injury is based on the impairment value;

generating a data package that includes data relating to the treatment plan and the impairment rating; and transmitting the data package to a destination.

14. The system of claim 13, wherein one or more pre-existing injuries of the worker are stored within the database.

15. The system of claim 13, wherein the database is a HIPAA compliant database.

16. The system of claim 13, wherein the treatment plan comprises one or more clinician recommended therapies for an injury sustained by the worker.

17. The system of claim 13, wherein the reminder is sent to the one or more stakeholders if a therapy is not executed according to the treatment plan.

* * * * *